(12) United States Patent
Zala et al.

(10) Patent No.: US 8,535,717 B2
(45) Date of Patent: *Sep. 17, 2013

(54) PHARMACEUTICAL COMPOSITION

(75) Inventors: Yashoraj Rupsinh Zala, Mumbai (IN); Nitin Bhalachandra Dharmadhikari, Mumbai (IN)

(73) Assignee: Sun Pharma Advanced Research Company Limited, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 13/102,328

(22) Filed: May 6, 2011

(65) Prior Publication Data

US 2011/0207794 A1    Aug. 25, 2011

Related U.S. Application Data

(63) Continuation of application No. 11/884,770, filed as application No. PCT/IN2006/000059 on Feb. 22, 2006.

(30) Foreign Application Priority Data

Feb. 22, 2005   (IN) .......................... 196/MUM/2005

(51) Int. Cl.
*A61K 9/24*       (2006.01)
*A61K 31/40*      (2006.01)

(52) U.S. Cl.
USPC .......................................... 424/472; 514/424

(58) Field of Classification Search
USPC .......................................... 424/472; 514/424
See application file for complete search history.

(56) References Cited

U.S. PATENT DOCUMENTS

| 4,806,359 | A  |   | 2/1989  | Radebaugh et al. |
| 5,415,871 | A  | * | 5/1995  | Pankhania et al. ............ 424/468 |
| 6,221,393 | B1 |   | 4/2001  | Collaueri et al. |
| 2004/0121015 | A1 |   | 6/2004  | Chidlaw et al. |
| 2004/0180088 | A1 |   | 9/2004  | Dudhara et al. |
| 2005/0202088 | A1 |   | 9/2005  | Hanshermann et al. |
| 2005/0250838 | A1 |   | 11/2005 | Challapalli et al. |
| 2006/0165796 | A1 |   | 7/2006  | Kshirsagar et al. |
| 2006/0204578 | A1 | * | 9/2006  | Vergez et al. ................. 424/473 |
| 2007/0298098 | A1 | * | 12/2007 | Jenkins et al. ................ 424/456 |
| 2009/0123541 | A1 | * | 5/2009  | Zala et al. ..................... 424/472 |
| 2011/0206767 | A1 | * | 8/2011  | Zala et al. ..................... 424/465 |

FOREIGN PATENT DOCUMENTS

| EP | 1 118 321 A1 | 7/2001 |
| WO | 01/51033 A1 | 7/2001 |
| WO | 03/101428 A1 | 12/2003 |
| WO | 2006/080029 A1 | 8/2006 |

* cited by examiner

*Primary Examiner* — Aradhana Sasan
(74) *Attorney, Agent, or Firm* — Sughrue Mion, PLLC

(57) ABSTRACT

The present invention relates to an oral controlled release pharmaceutical composition in the form of a unit dosage form comprising:
(a) a highly soluble high dose active ingredient consisting essentially of therapeutically effective amount of levetiracetam or a pharmaceutically acceptable derivative thereof, and
(b) a rate controlling means comprising a rate-controlling agent and/or a coating selected from (i) a active ingredient permeable coating surrounding the unit dosage form, and (ii) an active ingredient impermeable coating covering one or more surfaces but not all the surfaces of the unit dosage form, wherein the composition is in the form of a compact tablet and the levetiracetam or a pharmaceutically acceptable derivative thereof is present in an amount ranging from about 55% to about 90% by weight of the tablet.

8 Claims, No Drawings

PHARMACEUTICAL COMPOSITION

CROSS REFERENCE TO RELATED APPLICATION

This is a continuation application of U.S. application Ser. No. 11/884,770 filed Aug. 21, 2007, which is a 371 application of PCT/IN2006/000059 filed Feb. 22, 2006, which in turn claims priority to Indian Application No. 196/MUM/2005 filed Feb. 22, 2005. The above-noted applications are incorporated herein by reference in their entirety.

TECHNICAL FIELD

The present invention relates to an oral pharmaceutical composition for controlled release of levetiracetam or its pharmaceutically acceptable derivative thereof for use in the treatment of epileptic seizures.

BACKGROUND OF THE INVENTION

Levetiracetam is indicated as adjunctive therapy in the treatment of partial onset seizures in adults with epilepsy. In clinical trials, daily doses of 1000 mg, 2000 mg and 3000 mg, given as twice-daily dosing, were shown to be effective. It is recommended that such treatments should be initiated with a daily dose of 1000 mg/day, given as twice-daily dosing (500 mg BID). Additional dosing increments may be given so as to reach a maximum recommended daily dose of 3000 mg. The currently commercially available tablets are available in strengths of 250 mg, 500 mg and 750 mg of levetiracetam making it very inconvenient for the patient to comply with the dosing regimen prescribed by the physician particularly when the patient may be stabilized at the higher daily dose.

Sustained or controlled release compositions have not been prepared and made available herebefore. In order to reduce dosing frequency, to improve patient compliance to dosing regimen, as well as to reduce peak related side effects there is a need to provide a controlled release composition of levetiracetam in a compact unit dosage form that is easily swallowable and releases levetiracetam in a controlled manner preferably at a uniform controlled rate. Controlling the rate of release of levetiracetam from a unit dosage form containing high amounts of about 500 mg to 1000 mg per tablet for twice daily dosing or containing 1000 mg to 1500 mg for once-daily dosing is a problem because of (a) A very high solubility (104 g/100 ml) of levetiracetam which can not be decreased by altering the pH of the microenvironment and (b) the requirement to have compact tablets that are easily swallowable precludes the use of known controlled release systems that use a large quantity of excipients including rate-controlling agents.

The problem lies in not only slowing the rate of release of levetiracetam with a solubility as high as 104 g/100 ml from a compact dosage form but also providing a reproducible release at a controlled rate preferably uniform zero order rate while using very low amounts of rate-controlling agents.

WO00151033 ('033 application) discloses an oral solid pharmaceutical controlled release composition comprising excipients selected from inert, absorbent or lipidic matrices or mixtures thereof, an enterosoluble polymer and alkalizing agent. The alkalizing agent creates a microenvironment of higher pH in which the unionized less soluble pseudoephedrine is present in larger proportions and this contributes to the slower release. On the other hand the levetiracetam of the present invention is highly soluble in its unionized form itself, making the invention disclosed in '033 application unsuitable for the slow, controlled delivery of levetiracetam.

OBJECTS OF THE INVENTION

It is an object of the present invention to provide a pharmaceutical composition for controlled release comprising levetiracetam or a pharmaceutically acceptable derivative thereof.

It is another object of this invention to provide a once-a-day controlled release pharmaceutical composition comprising levetiracetam or a pharmaceutically acceptable derivative thereof.

It is yet another object of the present invention to provide a compact dosage form comprising high daily doses of levetiracetam or a pharmaceutically acceptable derivative thereof.

SUMMARY OF THE INVENTION

We have found that a compact, controlled release pharmaceutical composition of levetiracetam or a pharmaceutically acceptable derivative thereof can be successfully obtained. The pharmaceutical composition of the present invention can be suitably designed to provide controlled release compositions that control release over prolonged periods of time, such as over 8, 12 or 24 hours after oral administration.

Accordingly, the present invention resolves the aforesaid problems associated with preparation of oral controlled release pharmaceutical composition of levetiracetam and provides in its various embodiments the following:

A. An oral controlled release pharmaceutical composition in the form of a unit dosage form comprising:

(a) a highly soluble high dose active ingredient consisting essentially of therapeutically effective amount of levetiracetam or a pharmaceutically acceptable derivative thereof, and (b) a rate controlling means comprising a rate-controlling agent and/or a coating selected from an (i) active ingredient permeable coating surrounding the unit dosage form, and (ii) an active ingredient impermeable coating covering one or more surfaces, but not all the surfaces, of the unit dosage form, wherein the composition is in the form of a compact tablet and the levetiracetam or a pharmaceutically acceptable derivative thereof is present in an amount ranging from about 55% to about 90% by weight of the tablet.

B. An oral controlled release pharmaceutical composition in the form of a unit dosage form as in A wherein the composition releases the active ingredient at a substantially uniform rate to provide therapeutically effective plasma levels of levetiracetam upon oral administration to a human subject.

C. An oral controlled release pharmaceutical composition in the form of a unit dosage form as in A wherein the levetiracetam or a pharmaceutically acceptable derivative thereof is present in an amount ranging from about 70% to about 85% by weight of the tablet.

D. A once-daily oral controlled release pharmaceutical composition in the form of a unit dosage form comprising:

(a) a highly soluble high dose active ingredient consisting essentially of therapeutically effective single daily dose of levetiracetam or a pharmaceutically acceptable derivative thereof, and (b) A rate controlling means comprising a rate-controlling agent and/or a coating selected from (i) an active ingredient permeable coating surrounding the unit dosage form, and (ii) an active ingredient impermeable coating covering one or more surfaces, but not all the surfaces, of the unit dosage form, wherein the composition releases the active ingredient at a substantially uniform rate.

E. A once-daily oral controlled release pharmaceutical composition in the form of a unit dosage form as in D wherein said rate is on an average in the range from about 3% to about 9% per hour.

F. An oral controlled release pharmaceutical composition in the form of a unit dosage form as in D wherein the composition is in the form of a compact tablet and the levetiracetam or a pharmaceutically acceptable derivative thereof is present in an amount ranging from about 55% to about 90% by weight of the tablet.

G. An oral controlled release pharmaceutical composition in the form of a unit dosage form as in F wherein the levetiracetam or a pharmaceutically acceptable derivative thereof is present in an amount ranging from about 70% to about 85% by weight of the tablet.

H. A once-daily oral controlled release pharmaceutical composition in the form of a unit dosage form as in D wherein levetiracetam or a pharmaceutically acceptable derivative thereof is present in an amount equivalent to about 1000 mg of levetiracetam.

I. An oral controlled release pharmaceutical composition in the form of a unit dosage form as in A wherein the rate-controlling agent is present in an amount ranging from about 1% to about 20% by weight of the composition J. A once-daily oral controlled release pharmaceutical composition in the form of a unit dosage form as in D wherein the rate-controlling agent is present in an amount ranging from about 1% to about 20% by weight of the composition K. An oral controlled release pharmaceutical composition in the form of a unit dosage form as in A wherein the active ingredient is present in a first and second compartment and the rate-controlling means is a rate-controlling agent present in the second compartment, the first compartment comprising the active ingredient and pharmaceutically acceptable excipients and the second compartment comprising the active ingredient and the rate-controlling agent, the first compartment providing rapid release of the active ingredient and the second compartment providing controlled release of the active ingredient.

L. An oral controlled release pharmaceutical composition in the form of a unit dosage form as in A or D wherein the rate-controlling agent is selected from the group comprising water-soluble hydrophilic polymers, water-insoluble hydrophobic polymers, hydrophobic excipients and mixtures thereof.

M. An oral controlled release pharmaceutical composition in the form of a unit dosage form as in A wherein the rate-controlling agent is xanthan gum.

N. A once-daily oral controlled release pharmaceutical composition in the form of a unit dosage form as in D wherein the rate-controlling agent is xanthan gum.

O. An oral controlled release pharmaceutical composition in the form of a unit dosage form as in M wherein the xanthan gum has a particle size such that 100% of the particles are less than 180 μm in size.

P. A once-daily oral controlled release pharmaceutical composition in the form of a unit dosage form as in N wherein the xanthan gum has a particle size such that 100% of the particles are less than 180 μm in size.

Q. An oral controlled release pharmaceutical composition in the form of a unit dosage form as in A wherein the rate-controlling agent has a viscosity of a 1% w/v aqueous solution in the range of about 1000 to about 6000 mPa s.

R. A once-daily oral controlled release pharmaceutical composition in the form of a unit dosage form as in D wherein the rate-controlling agent has a viscosity of a 1% w/v aqueous solution in the range of about 1000 to about 6000 mPa s.

S. An oral controlled release pharmaceutical composition in the form of a unit dosage form as in A wherein the rate controlling means is an active ingredient impermeable coating covering one or more surfaces, but not all the surfaces, of the unit dosage form.

T. A once-daily oral controlled release pharmaceutical composition in the form of a unit dosage form as in D wherein the rate controlling means is an active ingredient impermeable coating covering one or more surfaces, but not all the surfaces of the unit dosage form.

U. An oral controlled release pharmaceutical composition in the form of a unit dosage form as in S wherein the "active ingredient impermeable coating covering one or more surfaces, but not all the surfaces" is generated upon contact of unit dosage form having a coating surrounding the dosage with an aqueous medium whereby the coating is removed from one or more of the surfaces but not from at least one of the remaining surfaces of the dosage form.

V. A once-daily oral controlled release pharmaceutical composition in the form of a unit dosage form as in T wherein the "active ingredient impermeable coating covering one or more surfaces, but not all the surfaces" is generated upon contact of unit dosage form having a coating surrounding the dosage with an aqueous medium whereby the coating is removed from one or more of the surfaces but not from at least one of the remaining surfaces of the dosage form.

W. An oral controlled release pharmaceutical composition in the form of a unit dosage form as in U wherein the coating is removed completely from one surface of the unit dosage form.

X. An oral controlled release pharmaceutical composition in the form of a unit dosage form as in U wherein the coating is removed partially from one surface of the unit dosage form.

Y. A once-daily oral controlled release pharmaceutical composition in the form of a unit dosage form as in V wherein the coating is removed completely from one surface of the unit dosage form.

Z. A once-daily oral controlled release pharmaceutical composition in the form of a unit dosage form as in V wherein the coating is removed partially from one surface of the unit dosage form.

Herinafter an embodiment of the present invention will be referred to by embodiment A to Z as referred to above.

DETAILED DESCRIPTION OF THE INVENTION

The pharmaceutical composition of the present invention releases therapeutically effective amount of levetiracetam or a pharmaceutically acceptable derivative thereof, a highly soluble high dose active ingredient, over a prolonged period of time and provides the opportunity for less frequent dosing, such as once-a-day or twice-a-day dosing, thereby providing advantages over currently available immediate release compositions.

The term "controlled release" as used herein means slow release of the active ingredient wherein substantially all of the active ingredient in the composition is released in 6 hours or more than 6 hours. It is not intended to be restricted to any particular kinetic pattern of release. "Substantially all of the active ingredient" means at least 95% by weight of the active ingredient.

The term "highly soluble high dose active ingredient" as used herein means an active ingredient whose solubility is greater than 50 g in 100 ml of water, and whose daily dose is at least 750 mg. Levetiracetam has a very high solubility of 104 g in 100 ml of water.

The term "rate-controlling agent" as used herein means a pharmaceutical excipient that when present in the composition results in a slower rate of release as compared to the release from an identical composition in which the agent is absent.

The term "substantially uniform rate" as used herein to describe preferred embodiments (embodiment D above) of the present invention means that the release occurs at a constant rate over the period from 2 hrs to 12 hrs with a deviation from the average release rate of less than 50%. In more preferred embodiments such as in Examples 5 and 6 the deviation is less than 20%.

The term "active ingredient impermeable coating" as used herein means a coating that allows water and small ions or molecules to permeate across it but does not permit the permeation of active ingredient across it.

The term "compact" as used herein means the active ingredient is present in an amount at least 55% by weight of the unit dosage form The term "biphasic release" means that there is a first period in which the active ingredient is released rapidly followed by a second period in which the active ingredient is released slowly or in a controlled manner.

Embodiments A and D allow a choice in selection of rate controlling means.

Matrix compositions: In certain compositions of the present invention the rate controlling means consists of a rate-controlling agent, which is present in admixture with the active ingredient and optionally other excipients. Such embodiments will be referred to herein as matrix compositions.

Diffusion-controlled membrane coated systems or reservoir systems: In certain embodiments the rate controlling means is an active ingredient permeable coating comprising a rate-controlling agent surrounding the unit dosage form and such embodiments will be referred to herein as diffusion-controlled membrane coated systems or reservoir systems. In such reservoir systems a rate-controlling agent may optionally also be present in admixture with the active ingredient and optionally other excipients. In certain embodiments of the present invention includes both of the above-mentioned rate controlling means i.e. a rate-controlling agent which is present in admixture with the active ingredient and optionally other excipients as well as an active ingredient permeable coating.

Wrap-matrix systems: In certain other more preferred embodiments of the present invention the rate controlling means is a combination of first means which is a rate-controlling agent which is present in admixture with the active ingredient and optionally other excipients and a second means which is an active ingredient impermeable coating covering one or more surfaces, but not all the surfaces, of the unit dosage form. Such embodiments will be referred to herein as wrap-matrix systems.

Now, the present invention in its various embodiments is described herein below.

The pharmaceutical composition of the present invention provides therapeutically effective plasma levels of levetiracetam upon oral administration once-daily or twice-daily to a human subject.

The levetiracetam or a pharmaceutically acceptable derivative thereof may be present in amounts ranging from about 500 mg to about 1600 mg, equivalent to weight of levetiracetam; preferably from about 700 mg to about 1000 mg, equivalent to weight of levetiracetam.

In accordance with the present invention, embodiment A comprising a therapeutically effective amount of levetiracetam or a pharmaceutically acceptable derivative thereof is in the form of a compact tablet, wherein the levetiracetam or a pharmaceutically acceptable derivative thereof is present in an amount ranging from about 55% to about 90% by weight of the tablet. Preferably, the levetiracetam or a pharmaceutically acceptable derivative thereof is present in an amount ranging from about 70% to about 85% by weight of the tablet (Preferred embodiment C).

One embodiment of the present invention provides an oral controlled release pharmaceutical composition in the form of a unit dosage form comprising levetiracetam or a pharmaceutically acceptable derivative thereof, which releases the active ingredient at a substantially uniform rate so as to provide therapeutically effective plasma levels of levetiracetam upon oral administration to a human subject. In another preferred embodiment, the active ingredient is released at a substantially uniform release rate, which on an average, is in the range of from about 3% to about 9% per hour. Such a dosage form, for example, may be suitable for once-daily dosing of a high daily dose of 1000 mg of levetiracetam.

The release of levetiracetam or a pharmaceutically acceptable derivative thereof is controlled with the use of a rate controlling means comprising a rate-controlling agent and/or a coating selected from (i) an active ingredient permeable coating surrounding the unit dosage form, and (ii) an active ingredient impermeable coating covering one or more surfaces, but not all the surfaces, of the unit dosage form.

The rate-controlling agent may be present in admixture with the active ingredient. It may be present in the coating when the coating is a permeable coating surrounding the unit dosage form and is used as a means for controlling the rate, such as that in Example 2. The rate-controlling agent that may be used in admixture with the active ingredient may be selected from the group comprising water-soluble hydrophilic polymers, water-insoluble hydrophobic polymers, hydrophobic excipients and mixtures thereof. Examples of suitable water-soluble polymers include, but are not limited to, hydroxypropylcellulose, hydroxypropylmethyl cellulose, methyl cellulose, vinyl acetate copolymers, polysaccharides (such as alginate, xanthan gum and the like), polyethylene oxide, methacrylic acid copolymers, maleic anhydride/methyl vinyl ether copolymers and derivatives and mixtures thereof. The water-soluble polymer may be present in combination with a hydrophobic excipient as is illustrated in Example 1 (matrix composition) and in Example 2 where xanthan gum together with hydrogenated vegetable oil form the rate controlling agent. Similarly in Examples of suitable water-insoluble polymers include, but are not limited to, acrylates, cellulose derivatives such as ethylcellulose or cellulose acetate, methacrylates, acrylic acid copolymers and high molecular weight polyvinylalcohols. Examples of hydrophobic excipients include, but are not limited to, a natural fat (for example coconut, soya, cocoa) as such or totally or partially hydrogenated, beeswax, polyethoxylated beeswax, a mono-, bi- or tri-substituted glyceride, glyceryl palmitostearate, glyceryl behenate, diethyleneglycol palmitostearate, a polyethyleneglycol stearate, a polyoxyethyleneglycol palmitostearate, glyceryl monopalmitostearate, cetyl palmitate, polyethyleneglycol palmitostearate, mono- or di-glyceryl behenate, a fatty alcohol associated with a polyethoxylate fatty alcohol, cetyl alcohol, stearic acid, a saturated or unsaturated fatty acid or a hydrogenated derivative thereof, and/or hydrogenated castor oil.

The rate-controlling agent used is preferably a rate-controlling polymer. When the rate-controlling polymer is used in admixture with the active ingredient, preferably it has a viscosity greater than 1000 mPa s, more preferably between 1000 mPa s and 6000 mPa s. When the rate-controlling polymer is used to form the permeable coating surrounding the unit dosage form, the polymer has a viscosity of less than 100 mPa s. Examples of polymers uses for forming permeable coatings are known in the art.

The amount of the rate-controlling agent that may be used in the composition of the present invention is in the range from about 1% to about 50% by weight of the composition. Pereferably from about 1% to about 20% by weight of the composition such that a compact unit dosage form is obtained.

In one embodiment of the present invention, xanthan gum is used as the rate-controlling agent in amounts ranging from about 1% to about 20% by weight of the composition, preferably from about 1% to about 10% by weight of the composition. Xanthan gum exhibits a viscosity of 1200-1600 mPa s for a 1% w/v aqueous solution, at 25° C. It is available in various grades with different particle sizes; for example, Keltrol CG has a particle size such that 100% of the particles are less than 180 µm in size; Keltrol CGF has a particle size wherein 100% of the particles are less than 75 µm in size; Rhodigel has a particle size such that 100% of the particles are less than 250 µm, and 95% of the particles are less than 177 µm in size; Rhodigel 200 has a particle size wherein 100% of the particles are less than 177 µm, and 92% of the particles are less than 74 µm in size.

In embodiment K which is one embodiment of the matrix composition the composition has two compartments both comprising active ingredient. In the first compartment composition there is no rate controlling agent and the active ingredient is rapidly released whereas the second compartment composition the rate controlling agent provides controlled release of the active ingredient. Thus, a biphasic release of the active ingredient is obtained.

In preferred embodiments such as embodiment D the present invention provides a substantially uniform rate of release of the active ingredient. The composition according to this embodiment may be in the form of a compact tablet comprising a core and a coat. The coat may be selected from an active ingredient permeable coat surrounding the dosage form (as illustrated in Example 2) and an active ingredient impermeable coating covering one or more surfaces but not all the surfaces of the unit dosage form (as illustrated in Examples 3 to 6). The active ingredient permeable coating may be provided on a core by mixing the active ingredient with pharmaceutically acceptable excipients and optionally, a rate-controlling agent, compressing the mixture into a core, and coating the core with a coating composition comprising a rate-controlling agent. The rate-controlling agent that may be used to obtain the coating composition may be selected from the group consisting of water-soluble polymers/agents, water-insoluble polymers, pH dependent polymers and mixtures thereof. Examples of water-insoluble polymers and pH-dependent polymers that may be used include, but are not limited to, water-insoluble cellulose derivatives such as ethyl cellulose, and various grades of methacrylic acid copolymers, the different grades being dependent on the methacrylic acid content and the viscosity of the methacrylic acid polymers. Examples of water-soluble polymers/agents include, but are not limited to, methyl cellulose, hydroxypropyl methylcellulose, hydroxyethyl cellulose, hydroxypropyl cellulose, polyvinylpyrrolidone, polyethylene glycol, sugars, amino acids, bulking agents such as polydextrose, organic acids or salts thereof, glycerin, glycols, and the like. Preferred examples include monosaccharides, disaccharides such as lactose or sucrose, glycerine, propylene glycol, or salts thereof, sugar alcohols, polydextrose and the like, and mixtures thereof.

Herein below is described a more preferred embodiment (wrapmatrix system) of a once-daily oral controlled release pharmaceutical composition in the form of a unit dosage form comprising:

(a) a highly soluble high dose active ingredient consisting essentially of therapeutically effective single daily dose of levetiracetam or a pharmaceutically acceptable derivative thereof, and (b) A rate controlling means comprising a rate-controlling agent and an active ingredient impermeable coating covering one or more surfaces, but not all the surfaces, of the unit dosage form, wherein the composition releases the active ingredient at a substantially uniform rate.

In these more preferred embodiments there is a core in the form of a compressed bilayer tablet, the two layers being laminar, with the first layer comprising a pharmaceutically acceptable carrier capable of swelling upon imbibition of aqueous fluids, and the second layer comprising levetiracetam or a pharmaceutically acceptable derivative thereof in admixture with a sufficient quantity of a rate-controlling agent.

The first layer is a swellable composition and comprises a swellable agent that may be selected from a group comprising a swellable excipient, a gas generating agent and mixtures thereof. The swellable agent is generally used in an amount ranging from about 0.5% to about 95% by weight of the swellable composition. The swellable excipient that may be used may be a highly swellable excipient selected from vinylpyrrolidone polymers such as crospovidone; cellulose and cellulose derivatives such as carboxyalkyl celluloses, crosslinked carboxyalkylcelluloses and their alkali salts; sodium starch glycolate, starch and starch derivatives, resins and mixtures thereof. The highly swellable excipient is preferably used in an amount ranging from about 2% to about 35% by weight of the swellable composition. The swellable excipient that may be used may be a moderately swellable excipient and may be used in an amount ranging from about 5% to about 70% by weight of the swellable composition, preferably about 50% to about 70% by weight of the swellable composition. Gas generating agents that may be used in the present invention include carbonates such as calcium carbonate, bicarbonates such as sodium or potassium bicarbonate, sulfites such as sodium sulfite, sodium bisulfite, or sodium metabisulfite, and the like. These salts may be used alone or in combination with an acid source as a gas generating couple. The acid source may be an edible organic acid, a salt of an edible organic acid, acidic components such as acrylate polymers, or mixtures thereof. Examples of organic acids that may be used include citric acid, malic acid, succinic acid, tartaric acid, fumaric acid, maleic acid, ascorbic acid, glutamic acid, and their salts, and mixtures thereof.

The swellable composition may further comprise a wicking agent in an amount ranging from about 0.5% to about 10% by weight of the swellable composition. Examples of wicking agents that may be used include, but are not limited to, colloidal silicon dioxide, kaolin, titanium dioxide, fumed silicon dioxide, alumina, niacinamide, sodium lauryl sulfate, low molecular weight polyvinylpyrrolidone, m-pyrol, bentonite, magnesium aluminum silicate, polyester, polyethylene. Preferably, the wicking agents used in the pharmaceutical composition of the present invention include cellulose and cellulose derivatives, colloidal silicon dioxide, and mixtures thereof.

The swellable composition may also comprise osmogents in an amount ranging from about 0.5% to about 10% by weight of the swellable composition. Examples of osmogents that may be used include, but are not limited to, inorganic salts such as magnesium chloride or magnesium sulfate, lithium, sodium or potassium chloride, lithium, sodium or potassium hydrogen phosphate, lithium, sodium or potassium dihydrogen phosphate, salts of organic acids such as sodium or potassium acetate, magnesium succinate, sodium benzoate, sodium citrate or sodium ascorbate; carbohydrates such as mannitol, sorbitol, arabinose, ribose, xylose, glucose, fructose, mannose, galactose, sucrose, maltose, lactose, raffinose; water-soluble amino acids such as glycine, leucine, alanine, or methionine; urea and the like; osmopolymers selected from the group consisting of poly(hydroxyalkyl methacrylate) having a molecular weight of 20,000 to 5,000,000; poly(vinylpyrrolidone) having a molecular weight of about 10,000 to 360,000; poly(vinyl alcohol) having a low acetate content and lightly crosslinked with glyoxal, formaldehyde, glutaraldehyde and having a degree of polymerization from 2,000 to 30,000; poly(ethylene oxide) having a molecular weight from 10,000 to 7,8000,000; acidic carboxy polymers known as carboxypolymethylene or as carboxyvinyl polymers, a polymer consisting of acrylic acid lightly cross-linked with polyallylsucrose and sold under the trademark Carbopol®, acidic carboxy polymer having a molecular weight of 200,000 to 6,000,000, including sodium acidic carboxyvinyl hydrogel and potassium acidic carboxyvinyl hydrogel; Cyanamer® polyacrylamide; and the like, and mixtures thereof.

Pharmaceutically acceptable excipients such as diluents, buffers, lubricants and the like, in amounts and grades conventional to the pharmaceutical art, may be used to obtain the swellable composition. The swellable composition may be obtained by conventional processes known to a person of skill in the art, such as by granulating a mixture of all the components and using the granules thus obtained to prepare the first layer of the tablet core. Granulation may be wet granulation, or dry granulation.

The second layer of the tablet core comprises levetiracetam or a pharmaceutically acceptable derivative thereof in admixture with a sufficient quantity of a rate-controlling agent and optionally other excipients. The amount and type of the rate-controlling agent that may be used has been described above.

In these more preferred embodiments an active ingredient impermeable coating covering one or more surfaces, but not all the surfaces, of the unit dosage form, is provided.

The impermeable coating can be applied on selected surfaces of the core by compressing a dry coating composition onto the core or by immersing the core in a liquid coating composition, or by spray coating the selected surface or surfaces. The active ingredient is released from the uncoated surface at a uniform rate when the unit dosage form is placed in an aqueous medium or in the gastrointestinal fluids.

Alternatively, and more preferably the impermeable covering one or more surfaces, but not all the surfaces, of the unit dosage form, is provided in-situ as described in WO 2005039481. An impermeable coating is applied on the core so as to surround the tablet core and when the dosage form is placed in an aqueous medium the coating ruptures. Such coatings as described in WO 2005039481 may be used in this more preferred embodiment of the present invention and the methods so described therein may be used to obtain such impermeable coating.

The impermeable coating composition surrounding the tablet core comprises a film former, a plasticizer and other excipients. The film former may be selected from the group comprising water-insoluble polymers, water-soluble compounds and mixtures thereof. The core is coated to a weight gain of about 8% to about 15%.

The water-insoluble polymers that may be used in the impermeable coating composition include, but are not limited to, cellulose derivatives such as cellulose acetate, ethyl cellulose and the like, polyvinyl esters, polyvinyl acetals, polyacrylic acid esters, butadiene styrene copolymers, methacrylic and acrylate polymers, and mixtures thereof. The water-insoluble polymer is in the form of an aqueous latex dispersion. By "latex dispersion" is meant a synthetic resin dispersion in water. It is a durable milky dispersion of solid particles of the water insoluble polymer having an average particle size of 0.2-3 microns. It is similar to natural rubber latex. As an aqueous synthetic resin dispersion for the coating composition according to the present invention, any of the pharmacologically compatible, water-insoluble polymeric film formers described hereinabove may be used. Thus, for example, there can be used aqueous dispersions of any of the aforementioned water-insoluble polymers, including latex dispersions of polyvinyl esters, polyvinyl acetals, polyacrylic acid esters, cellulose ethers, cellulose esters, butadiene styrene copolymers, methacrylic and acrylate polymers, and the like. Ethyl cellulose latex dispersion is most preferably used. Suitable latex dispersions of ethyl cellulose include those available under the tradenames AQUACOAT ECD-30® from FMC Corporation (Philadelphia, USA) and SURELEASE® from Colorcon (West Point, Pa.). AQUACOAT® is an aqueous polymeric dispersion of ethylcellulose and contains sodium lauryl sulfate and cetyl alcohol while SURELEASE® is an aqueous polymeric dispersion of ethyl cellulose and contains dibutyl sebacate, oleic acid, ammoniated water and fumed silica.

When the impermeable coating composition has only a water-insoluble polymer, a passageway is drilled in the core, on the side that has the first layer comprising the swellable composition. When the composition is placed in an aqueous medium, water enters through the passageway, thereby causing swelling of the first layer. This swelling causes the coating to rupture only on the side that has the swellable composition and therefore exposes a defined surface area for release of the active ingredient. The release of the active ingredient is therefore controlled by the exposed and limited surface area, as well as by the rate-controlling agent used in the second layer.

The water-soluble compounds that may be used in the impermeable coating composition of the present invention include, but are not limited to, methyl cellulose, hydroxypropyl methylcellulose, hydroxyethyl cellulose, hydroxypropyl cellulose, polyvinylpyrrolidone, polyethylene glycol, sugars, amino acids, bulking agents such as polydextrose, organic acids or salts thereof, glycerin, glycols, and the like. Preferred examples include monosaccharides, disaccharides such as lactose or sucrose, glycerine, propylene glycol, or salts thereof, sugar alcohols, polydextrose and the like, and mixtures thereof. Typically, these water-soluble compounds are used in combination with a water-insoluble polymer. The amount of the water-soluble polymer used is such that, in combination with the water-insoluble polymer, the coating composition becomes semipermeable in nature, thereby allowing fluids from the external environment to enter the composition. This causes swelling of the first layer comprising the swellable composition, thereby rupturing the coating on one side, as described above.

Examples of plasticizers used in the coating composition include diethylphthalate, triethyl citrate, triethyl acetyl citrate, triacetin, tributylcitrate, polyethylene glycol, glycerol, vegetable and mineral oils, maltodextrin and mixtures thereof, the like. The plasticizer may be present in the coating in amount ranging from about 0.01% to about 25% by weight and more preferably from about 5% to about 15% by weight based on the dry weight of the coating.

The impermeable coating may optionally include a lubricant. Examples of the lubricants include talc, calcium stearate, colloidal silicon dioxide, glycerin, magnesium stearate, aluminium stearate, or a mixture thereof.

The compositions of the present invention may be prepared by conventional methods known to persons of skill in the art and more particularly the most preferred embodiment as described above may be prepared by methods known by disclosure in WO 2005039481.

The examples that follow do not limit the scope of the invention and are merely used as illustrations.

Example 1

The following example illustrates embodiment K of the present invention as claimed in claim 11. The composition is given in Table 1.

TABLE 1

| Ingredients | Quantity (mg/tablet) |
|---|---|
| First layer | |
| Intragranular additives | |
| Levetiracetam | 850.0 |
| Xanthan gum | 17.0 |
| Microcrystalline Cellulose (Avicel PH102) | 43.35 |
| Polyvinylpyrrolidone (PVP K-30) | 8.5 |
| Extragranular additives | |
| Hydrogenated vegetable oil (Lubritab) | 5.95 |
| Xanthan gum | 8.5 |
| Talc | 5.95 |
| Second layer | |
| Levetiracetam | 150.0 |
| Silicified microcrystalline cellulose (Prosolv, SMCC 90) | 127.2 |
| Colloidal silicon dioxide | 3.75 |
| Crospovidone | 15.0 |
| Sodium lauryl sulfate | 1.5 |
| FD&C blue lake No 1 | 0.6 |
| Magnesium stearate | 1.575 |
| Talc | 0.375 |
| Total tablet weight | ~1240 |

This example has levetiracetam in an amount 80.6% by weight of the composition.

The matrix composition was obtained as a bilayered tablet comprising 850 mg of levetiracetam in a first controlled-release layer, and 150 mg of levetiracetam in a second immediate-release layer, the composition thus providing a biphasic release of levetiracetam or its pharmaceutically acceptable salt, in the environment of use.

Aqueous granulation of a mixture of levetiracetam (850 mg), xanthan gum and microcrystalline cellulose, using PVP K-30 as the binder was carried out by conventional means. The granules thus obtained were lubricated with a mixture of lubritab, xanthan gum and talc, to obtain a first layer composition.

Levetiracetam (150 mg), Prosolv SMCC-90, colloidal silicon dioxide, crospovidone, sodium lauryl sulfate, color, magnesium stearate and talc were intimately mixed to obtain a second layer composition.

The first and second layer compositions were then compressed using capsule-shaped punches to obtain bilayered tablets.

Example 2

The following example illustrates an embodiment of the present invention wherein the rate controlling means is a combination of a rate-controlling agent and an active ingredient permeable coating surrounding the unit dosage form. A coated controlled release composition of levetiracetam was obtained in Table 2 as described below.

TABLE 2

| Ingredients | Quantity (mg/tablet) |
|---|---|
| Core | |
| Intragranular additives | |
| Levetiracetam | 750.0 |
| Xanthan gum | 15.0 |
| Microcrystalline Cellulose (Avicel PH102) | 38.25 |
| Polyvinylpyrrolidone (PVP K-30) | 7.5 |
| Extragranular additives | |
| Hydrogenated vegetable oil (Lubritab) | 5.25 |
| Xanthan gum | 7.5 |
| Talc | 5.25 |
| Coat | |
| Ethyl cellulose | Coated to a weight gain of about 9% |
| Hydroxypropyl methylcellulose (HPMC 3cps) | |
| Triacetin | |
| Polyethylene glycol (PEG 400) | |
| Total tablet weight | ~904 |

This example has levetiracetam in an amount 82.96% by weight of the composition.

Levetiracetam, xanthan gum and microcrystalline cellulose were wet granulated using an aqueous solution of PVP K-30. The granules were lubricated with a mixture of lubritab, xanthan gum and talc. The lubricated granules were then compressed to obtain the core of the tablet. The cores were coated with a coating solution comprising ethyl cellulose, HPMC (used in a ratio of ethylcellulose:HPMC of 70:30), triacetin and PEG 400 in a 1:4 mixture of methanol and dichloromethane, to a weight gain of about 9% by weight of the core.

Example 3

A controlled release composition of levetiracetam was obtained as described in Table 3 below.

TABLE 3

| Ingredients | Quantity (mg/tablet) |
|---|---|
| First layer | |
| Levetiracetam | 1000.0 |
| Polyvinylpyrrolidone (PVP K-30) | 10.0 |
| Xanthan gum | 20.0 |
| Microcrystalline cellulose (Avicel PH 102) | 51.0 |
| Talc | 7.0 |

TABLE 3-continued

| Ingredients | Quantity (mg/tablet) |
|---|---|
| Magnesium stearate | 7.0 |
| *Second layer* | |
| Silicified microcrystalline cellulose (Prosolv SMCC 90) | 84.8 |
| Colloidal silicon dioxide | 2.5 |
| Crospovidone 10.0 | 10.0 |
| Sodium lauryl sulfate | 1.0 |
| FD&C blue lake No 1 | 0.40 |
| Magnesium stearate | 1.05 |
| Talc | 0.25 |
| *Coat* | |
| Ethyl cellulose (as aqueous dispersion Aquacoat ®) Dibutyl sebacate | Coated to a weight gain of about 12% by weight |
| Total tablet weight | ~1340 |

This example has levetiracetam in an amount 74.62% by weight of the composition.

The first layer composition was obtained by carrying out aqueous wet granulation of a mixture of levetiracetam, PVP K-30, xanthan gum and Avicel. The granules thus obtained were lubricated with talc and magnesium stearate to obtain a first blend.

The second layer composition was obtained by intimately mixing silicified microcrystalline cellulose (Prosolv), colloidal silicon dioxide, crospovidone, sodium lauryl sulfate, color, magnesium stearate and talc.

The two layers were compressed to obtain bilayered tablets. These tablets were then coated with a coating composition comprising an aqueous dispersion of ethyl cellulose and dibutyl sebacate to a weight gain of about 12% by weight of the bilayered core.

Upon contact with an aqueous environment, the second layer swells to exert pressure on the ethyl cellulose coating, thereby rupturing the coating only on one side, i.e. the ethyl cellulose coating on the side of the tablet comprising the second layer ruptures, while the coating on the other surfaces of the tablet is intact. This selected rupture on one side of the tablet provides a defined and controlled surface area for release of levetiracetam.

Example 4

A controlled release composition of levetiracetam was obtained as described in Table 4 below.

TABLE 4

| Ingredients | Quantity (mg/tablet) |
|---|---|
| *First layer* | |
| Intragranular additives | |
| Levetiracetam | 1000.0 |
| Polyvinylpyrrolidone (PVP K-90F) | 15.0 |
| Polyvinylpyrrolidone (PVP K-30) | 10.0 |
| Extragranular additives | |
| Magnesium stearate | 6.0 |
| Talc | 6.0 |
| *Second layer* | |
| Silicified microcrystalline cellulose | ~30 |
| Crospovidone | |

TABLE 4-continued

| Ingredients | Quantity (mg/tablet) |
|---|---|
| Sodium lauryl sulfate | |
| Colloidal silicon dioxide | |
| Magnesium stearate | |
| *Coat* | |
| Ethyl cellulose (as aqueous dispersion Aquacoat ®) Dibutyl sebacate | Coated to a weight gain of about 8% by weight |

This example has levetiracetam in an amount 86.8% by weight of the composition.

Levetiracetam, PVP K-90F and PVP K-30 were mixed and granulated with water to obtain granules, which were lubricated with magnesium stearate and talc. Silicified microcrystalline cellulose, crospovidone, sodium lauryl sulfate, colloidal silicon dioxide and magnesium state were separately mixed and compressed using 3.5 mm round punches to obtain a second layer composition, which was further compressed with the levetiracetam-containing granules such that an in-lay tablet is obtained. This tablet is then coated with a coating composition comprising an aqueous dispersion of ethyl cellulose and dibutyl sebacate to a weight gain of about 8% by weight of the core.

The in-lay portion of the tablet comprising the second layer is capable of swelling upon contact with an aqueous medium, thereby causing a rupture of the external ethyl cellulose coating, on that side of the tablet that comprises the openable layer. This rupture exposes a specific surface area of the tablet from where the release of levetiracetam takes place, i.e. the ethyl cellulose coating remains intact on the rest of the tablet surfaces. Thus, this composition controls release of levetiracetam by controlling the surface area of release, the surface area being dependent on the dimensions of the second layer composition, which forms the in-lay tablet.

Examples 5 and 6

A controlled release composition of levetiracetam was obtained as described in Table 5 below.

TABLE 5

| | Quantity (mg/tablet) | |
|---|---|---|
| Ingredients | Example 5 | Example 6 |
| *First layer* | | |
| Levetiracetam | 1000 | 1000 |
| Polyvinylpyrrolidone (PVP K-30) | 10.0 | 10.0 |
| Xanthan gum | 15.0 | 12.5 |
| Microcrystalline cellulose (Avicel PH 102) | 51.0 | 51.5 |
| Talc | 7.0 | 7.0 |
| Magnesium stearate | 7.0 | 7.0 |
| *Second layer* | | |
| Silicified microcrystalline cellulose (Prosolv SMCC 90) | 84.8 | 79.8 |
| Colloidal silicon dioxide | 2.5 | 2.5 |
| Crospovidone XL 10 | 10.0 | 15.0 |
| Sodium lauryl sulfate | 1.0 | 1.0 |
| FD&C blue lake No 1 | 0.40 | 0.40 |
| Magnesium stearate | 0.25 | 0.25 |
| Talc | 0.25 | 0.25 |
| *Coat* | | |
| Ethyl cellulose | Coated to a weight gain of | |

TABLE 5-continued

| Ingredients | Quantity (mg/tablet) | |
|---|---|---|
| | Example 5 | Example 6 |
| (as aqueous dispersion Aquacoat ®) Dibutyl sebacate | about 12% by weight | |

These examples have levetiracetam in an amount of about 67% by weight of the composition.

The tablets of Examples 5 and 6 were obtained by a process similar to that in Example 1 above. These tablets were subjected to dissolution testing using pH 6.8 phosphate buffer as a dissolution medium in United States Pharmacopoeia dissolution apparatus, type 1, at a speed of 25 rpm. The results are recorded in Table 6 below.

TABLE 6

| | Percent drug released | |
|---|---|---|
| Time (hours) | Example 5 | Example 6 |
| 0 | 0 | 0 |
| 1 | 7 | 8 |
| 2 | 12 | 17 |
| 4 | 20 | 32 |
| 8 | 37 | 60 |
| 12 | 53 | 95 |
| 16 | 71 | 99 |
| 20 | 91 | 99 |

The release rate of levetiracetam from these compositions was calculated and is recorded in Table 7 below.

TABLE 7

| Time (t) (hrs) | Percent levetiracetam released (Q) | | $t_{avg} = (t_1 + t_2)/2$ | | Release rate $(\Delta Q/\Delta t) = (Q_2 - Q_1)/(t_2 - t_1)$ | |
|---|---|---|---|---|---|---|
| | Example 5 | Example 6 | Example 5 | Example 6 | Example 5 | Example 6 |
| 0 | 0 | 0 | — | — | — | — |
| 1 | 7 | 8 | 1.5 | 1.5 | 5.0 | 9.0 |
| 2 | 12 | 17 | | | | |
| 4 | 20 | 32 | 3.0 | 3.0 | 4.0 | 7.5 |
| 8 | 37 | 60 | 6.0 | 6.0 | 4.25 | 7.0 |
| 12 | 53 | 95 | 1.0 | 10.0 | 4.0 | 8.75 |
| 16 | 71 | 99 | 14.0 | 14.0 | 4.25 | — |
| 20 | 91 | 99 | 18.0 | 18.0 | 5.0 | — |
| Average release rate $(\Delta Q/\Delta t)_{avg}$ (% per hour) | | | | | 4.42 | 8.06 |

The above data demonstrates that the embodiment of the present invention according to claim 4 provides a substantially uniform rate of release. In these examples substantially uniform release occurs over the period from 2 hrs to 12 hrs with a deviation from the average release rate of less than 20%.

While the invention has been described by reference to specific embodiments, this was done for purposes of illustration only and should not be construed to limit the spirit or the scope of the invention.

What is claimed is:

1. A compact tablet comprising 55% to 90% by weight of levetiracetam or pharmaceutically acceptable derivative thereof, in an amount from 750 mg to 1600 mg, in admixture with a rate-controlling agent, wherein the tablet is suitable for once-a-day administration.

2. The compact tablet as described in claim 1, wherein the rate-controlling agent is selected from the group consisting of water-soluble hydrophilic polymers, water-insoluble hydrophobic polymers, hydrophobic excipients and mixtures thereof.

3. The compact tablet as described in claim 2, wherein the water soluble hydrophilic polymers are selected from the group consisting of hydroxypropylcellulose, hydroxypropylmethyl cellulose, methyl cellulose, vinyl acetate copolymers, polysaccharides, polyethylene oxide, methacrylic acid copolymers, maleic anhydride/methyl vinyl ether copolymers and derivatives and mixtures thereof.

4. The compact tablet as described in claim 2, wherein the water-insoluble hydrophobic polymers are selected from the group consisting of acrylates, ethylcellulose, cellulose acetate, methacrylates, acrylic acid copolymers and high molecular weight polyvinylalcohols and mixtures thereof.

5. The compact tablet as described in claim 2, wherein the hydrophobic excipients are selected from a natural fat, beeswax, polyethoxylated beeswax, a mono-, bi- or tri-substituted glyceride, glycerylpalmitostearate, glycerylbehenate, diethyleneglycolpalmitostearate, a polyethyleneglycol stearate, a polyoxyethyleneglycolpalmitostearate, glycerylmonopalmitostearate, cetylpalmitate, polyethyleneglycolpalmitostearate, mono- or di-glycerylbehenate, a fatty alcohol associated with a polyethoxylate fatty alcohol, cetyl alcohol, stearic acid, a saturated or unsaturated fatty acid or a hydrogenated derivative thereof, and/or hydrogenated castor oil and mixtures thereof.

6. The compact tablet as described in claim 2, wherein the rate-controlling agent is used in an amount ranging from 1 to 20% by weight of the compact tablet.

7. The compact tablet as described in claim 3, wherein the rate-controlling agent used is xanthan gum.

8. The compact tablet as described in claim 7, wherein the xanthan gum is used in an amount ranging from about 1% to about 20% by weight of the compact tablet.

* * * * *